United States Patent [19]
Eaton et al.

[11] Patent Number: 5,795,299
[45] Date of Patent: Aug. 18, 1998

[54] ULTRASONIC TRANSDUCER ASSEMBLY WITH EXTENDED FLEXIBLE CIRCUITS

[75] Inventors: John W. Eaton, Palo Alto; Randall L. Schlesinger, San Mateo; Michael H. Ikeda, San Jose; Charles W. Brummer, Simi Valley; Xavier L. Pacheco, Chatsworth; Robert Kevakian, Agoura Hills; Ricardo G. Espinosa, Milpitas, all of Calif.

[73] Assignee: Acuson Corporation, Mountain View, Calif.

[21] Appl. No.: 791,601

[22] Filed: Jan. 31, 1997

[51] Int. Cl.$^6$ .................................... A61B 8/00
[52] U.S. Cl. .................................... 600/459
[58] Field of Search ................... 128/660.1, 662.06; 600/446, 459; 361/749–50, 776

[56] References Cited

U.S. PATENT DOCUMENTS

| | | |
|---|---|---|
| 3,546,775 | 12/1970 | Lalmond et al. . |
| 4,193,965 | 3/1980 | Cullingford et al. . |
| 4,302,268 | 11/1981 | Tachiki et al. . |
| 4,435,614 | 3/1984 | McAusland . |
| 4,460,224 | 7/1984 | Stopper . |
| 4,587,719 | 5/1986 | Barth . |
| 4,647,131 | 3/1987 | Van Woensel . |
| 4,708,661 | 11/1987 | Morland et al. . |
| 4,794,931 | 1/1989 | Yock . |
| 4,824,379 | 4/1989 | Roberts et al. . |
| 5,130,499 | 7/1992 | Dijkshoorn . |
| 5,206,463 | 4/1993 | DeMaso et al. . |
| 5,227,008 | 7/1993 | Klun et al. . |
| 5,239,448 | 8/1993 | Perkins et al. . |
| 5,250,758 | 10/1993 | Fjelstad et al. . |
| 5,262,590 | 11/1993 | Lia . |
| 5,309,316 | 5/1994 | Yagi et al. . |
| 5,334,487 | 8/1994 | Kindl et al. . |
| 5,351,691 | 10/1994 | Brommersma .......... 128/662.06 |
| 5,368,037 | 11/1994 | Eberle et al. . |
| 5,373,109 | 12/1994 | Argyrakis et al. . |
| 5,398,689 | 3/1995 | Connor et al. . |
| 5,403,202 | 4/1995 | Roehling . |
| 5,414,220 | 5/1995 | Hanato et al. . |
| 5,418,691 | 5/1995 | Tokura . |
| 5,421,080 | 6/1995 | Bellavance et al. .......... 29/825 |
| 5,451,169 | 9/1995 | Corbett, III et al. . |
| 5,519,578 | 5/1996 | Fujii . |
| 5,525,760 | 6/1996 | Rohatgi et al. . |
| 5,552,565 | 9/1996 | Cartier et al. . |
| 5,622,175 | 4/1997 | Sudol et al. .......... 128/662.06 |

OTHER PUBLICATIONS

Specification of "Modular Transducer System", Serial No. 08/584,332 filed Jan. 5, 1996, Inventor: Vaughn R. Marian, Jr.

Specification of "Submersible Connector System", Serial No. 08/538,870 filed Oct. 4, 1995, Inventor: Vaughn R. Marian, Jr.

*Primary Examiner*—Francis Jaworski
*Attorney, Agent, or Firm*—Brinks Hofer Gilson & Lione

[57] ABSTRACT

An ultrasonic transducer assembly includes a conduit that defines a lumen, and the lumen carries a flexible circuit. The flexible circuit can take several forms. In one form the circuit is folded at first and second fold lines, and at least one of the folds is oriented obliquely to the longitudinal axis of conduit. In another form the flexible circuit includes an end portion that defines a plurality of substantially parallel grooves, each groove aligned with and exposing a respective one of the conductors of the circuit. Additional conductors are positioned in respective ones of the grooves and are electrically connected with the respective conductors of the flexible circuit.

35 Claims, 7 Drawing Sheets

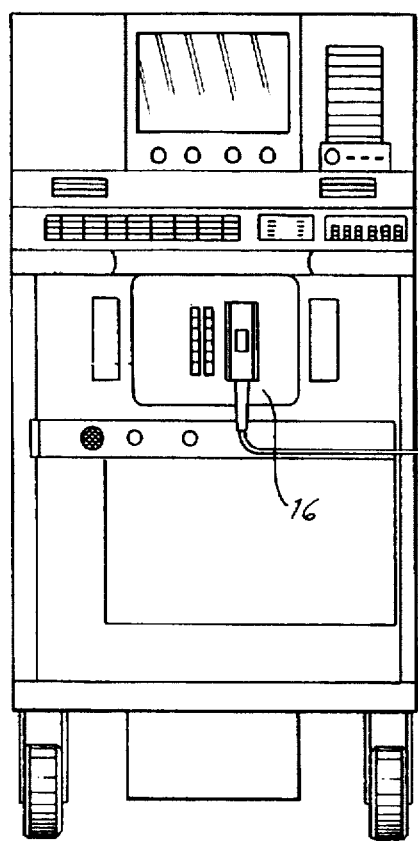
Fig. 1
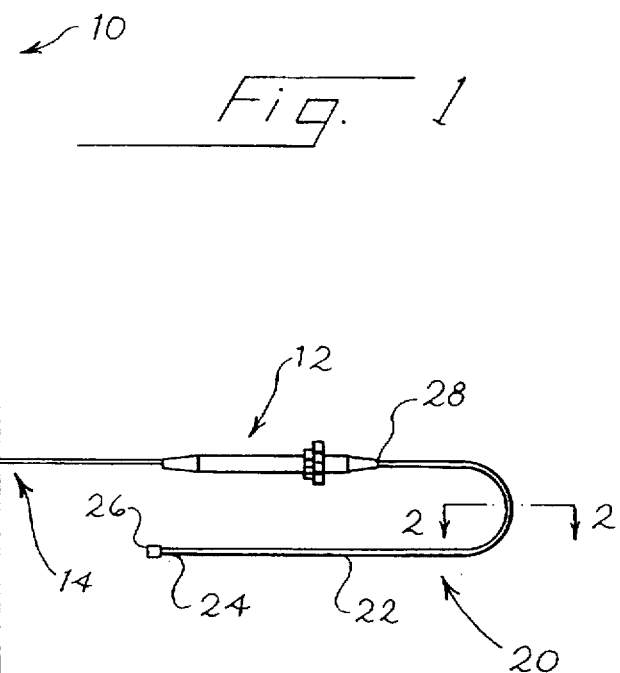
Fig. 2
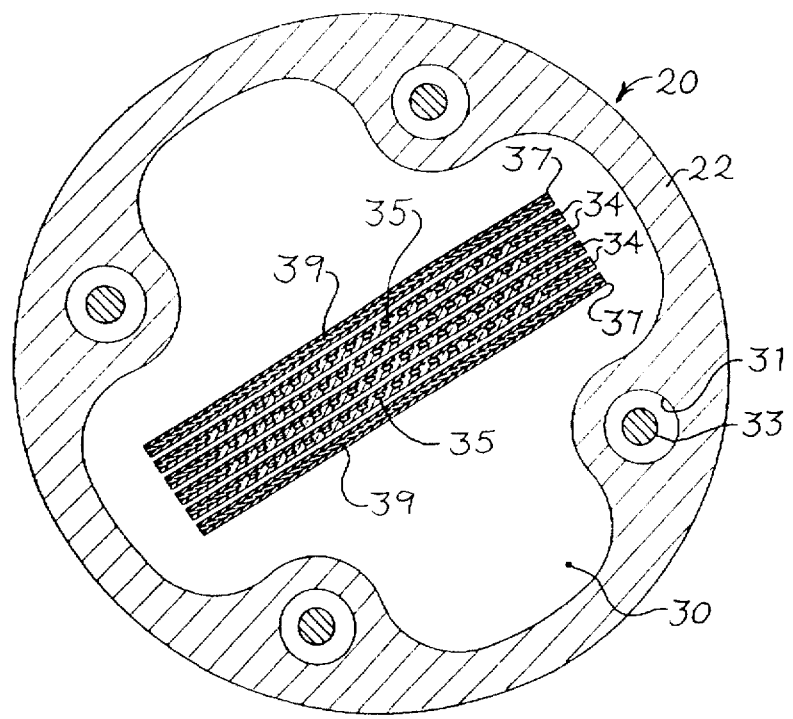

ULTRASONIC TRANSDUCER ASSEMBLY WITH EXTENDED FLEXIBLE CIRCUITS

BACKGROUND OF THE INVENTION

This invention relates to ultrasonic transducer assemblies which are placed within a body cavity to provide ultrasonic images. This invention is particularly directed to an improved extended flexible circuit suitable for use with such transducer assemblies.

Ultrasonic transducer assemblies take many forms, as appropriate for various applications. For example, the ultrasonic transducer assemblies used for assessing intravascular lesions such as stenosis and for monitoring the results of interventional therapy on such lesions are shaped as elongated catheters. See for example Yock U.S. Pat. No. 4,794,931 and Eberle U.S. Pat. No. 5,368,037. Such ultrasonic transducers are often single use, disposable devices, and they can provide any suitable image format, such as a radial format using phased array or rotating crystals.

Conner U.S. Pat. No. 5,398,689 discloses an ultrasonic transducer using a flexible circuit inside a sheath in a flexible shaft portion of the transducer assembly. Flexible circuits as described in the Conner patent suffer from the disadvantage that a typical substrate for a flexible circuit has a maximum length of about 19 inches in commercially available forms. Flexible circuits longer than this size can be made in a conveyor-type process, but in many cases the base insulating substrate layer is thicker than that desired for an ultrasonic transducer assembly, because of the stress imposed on the substrate layer in the conveyor system.

McAusland U.S. Pat. No. 4,435,614 discloses one folding geometry for forming elongated flexible circuit traces in an ultrasonic transducer assembly. The geometry illustrated in the McAusland patent suffers from the disadvantage that the folded regions of the flexible circuit provide increased thickness, and the illustrated geometry places these folded regions in positions where they will stack one on top of the other, thereby further increasing the maximum thickness of the flexible circuit.

A need presently exists for an improved ultrasonic transducer assembly having extended flexible circuits which have adequate length, and which can readily be configured to minimize the overall thickness of the flexible circuit in its final configuration.

SUMMARY OF THE INVENTION

This invention relates to ultrasonic transducer assemblies of the type having an elongated conduit, a plurality of ultrasonic transducer elements carried by the conduit, and a flexible circuit carried in the lumen of the conduit.

According to a first aspect of the invention, the flexible circuit comprises first, second and third portions. The first and second portions meet at a first fold; the second and third portions meet at a second fold; and at least one of the folds is oriented obliquely to the axis of the lumen.

According to a second aspect of this invention, an ultrasonic transducer assembly as described initially above includes an end portion for the flexible circuit. This end portion comprises an array of substantially parallel grooves, each groove aligned with and exposing a respective one of the conductors of the flexible circuit. A plurality of additional conductors are provided, each extending into a respective one of the grooves and electrically connected to the respective first-mentioned conductor. These additional conductors can be included in an additional flexible circuit or a ribbon cable, or they can be individually insulated. The grooves of the first-mentioned flexible circuit automatically align the additional conductors during assembly.

According to a third aspect of this invention, the signal-carrying conductors on flexible circuits in a catheter-mounted ultrasonic transducer assembly are disposed between and shielded by first and second shielding layers formed as respective flexible circuits.

The preferred embodiments of the invention will now be described with reference to the attached drawings.

BRIEF DESCRIPTION OF THE DRAWINGS

FIG. 1 is a front view of an ultrasonic imaging system which includes an ultrasonic transducer assembly that incorporates a presently preferred embodiment of this invention.

FIG. 2 is a cross-sectional view taken along line 2—2 of FIG. 1.

DETAILED DESCRIPTION OF THE PRESENTLY PREFERRED EMBODIMENTS

Figure 3:
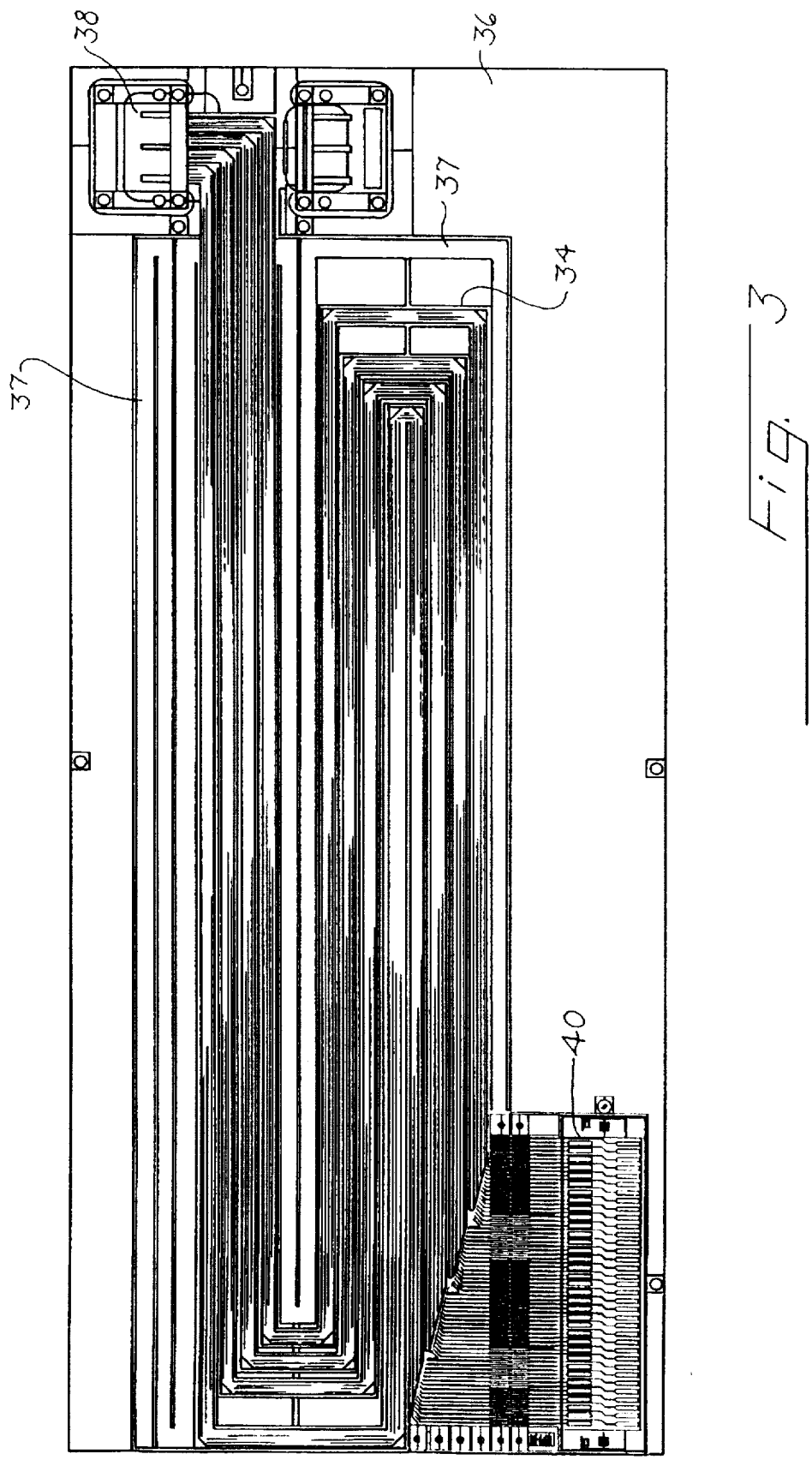
FIG. 3 is a plan view showing the original layout of the flexible circuit included in the embodiment of FIG. 1, prior to final folding and assembly.

Turning now to the drawings, FIG. 1 shows a front view of an ultrasound medical diagnostic imaging system 10 which incorporates the presently preferred embodiment of this invention. The imaging system 10 is coupled by a connector 16 and a cable 14 to a handle or control mechanism 12. All of the elements 10–16 are well known to those skilled in the art and can take any suitable form.

As shown in FIG. 1, the control mechanism 12 is connected to a transducer assembly 20, which includes a conduit 22 having a distal end 24 and a proximal end 28. The distal end 24 carries transducer elements 26, and the proximal end 28 may be releasably connected to the control mechanism 12. The connection system at the proximal end 28 may take the form described in U.S. patent application Ser. No. 08/792,291, assigned to the assignee of this invention. The transducer elements 26 can, for example, form a phased array having either a linear or a curvilinear shape. Preferably, the transducer elements 26 and the distal end of the catheter take the form described in U.S. patent application Ser. No. 08/791,598, also assigned to the assignee of this invention. The specifications of these two applications are hereby incorporated by reference in their entirety. Alternately, the control mechanism may be releasably connected to the cable 14.

As shown in FIG. 2, the conduit 22 defines a central lumen 30 that carries a plurality of flexible circuits 34. The flexible circuits 34 include separate conductors 35 which carry transmit signals from the imaging system 10 to the individual transducer elements 26, as well as echo signals from the transducer elements 26 to the imaging system 10. Flexible circuits 37 are positioned at the top and bottom of the stack of flexible circuits 34, and each flexible circuit 37 includes a full-surface shielding conductor 39.

The conduit 22 also defines four smaller lumens 31, which each carry a respective control wire 33. The control wires 33 transmit steering forces from the control mechanism 12 to the distal end 24 in the conventional manner. In this embodiment the transducer assembly 20 is intended for use in cardiac therapy or diagnosis and has a length of about 110 centimeters. Of course, other applications and lengths are possible. The flexible circuits 34 extend over this entire length, and thus have a length greater than that of a conventional flexible circuit substrate panel.

FIG. 3 shows a preferred layout for the flexible circuits 34, 37 on a substrate panel 36. In this embodiment the substrate panel is a conventional panel having a length of about 19 inches. As shown in FIG. 3, the flexible circuits 34 are laid out in a serpentine pattern such that the individual flexible circuits 34 have an overall length substantially greater than that of the substrate panel 36. As shown in FIG. 3, first and second connector regions 38, 40, are formed on the substrate panel 36, interconnected by the flexible circuits 34. The first connector region 38 is adapted for rapid and inexpensive connection to the transducer elements, and the second connector region 40 is adapted for releasable connection to the control mechanism 12 or the cable 14. In general, the conductors (not shown in FIG. 3) of the flexible circuits are parallel to the edges of the serpentine strips between the connector regions 38, 40. Preferably, ground return conductors are included as the laterally outermost conductors on both lateral edges of each conductor-bearing flexible circuit 34.

After the connector regions 38, 40 and the flexible circuits 34 have been formed on the substrate panel 36 in the conventional manner, the flexible circuits 34 are cut from the substrate panel 36 with parallel slits using a pulsed $CO_2$ laser, and then folded as described below. FIGS. 4–10 are schematic views that illustrate consecutive steps in the folding of a portion of one of the flexible circuits 34. For clarity, the entire length of the flexible circuit 34, the connector regions and the other bands of the flexible circuit are not shown in these figures.

Figure 4:
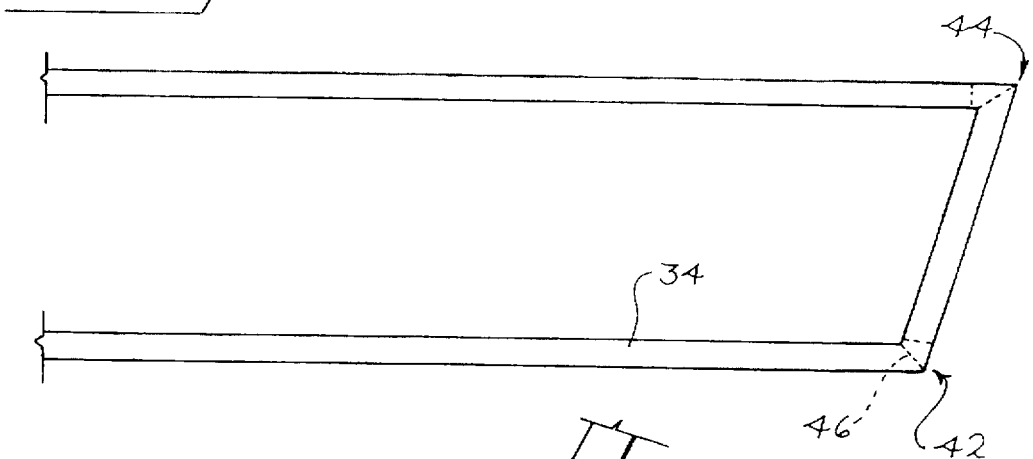
FIGS. 4 through 10 are consecutive views showing the manner in which an individual flexible circuit is folded prior to installation into the lumen of FIG. 2.

Turning to FIG. 4, the flexible circuit 34 is shown after it has been cut from the substrate panel, but prior to any folding. This flexible circuit 34 may carry 16 or more parallel insulated conductors, depending on the application. These conductors form first and second corners 42, 44, each at an angle of substantially 90 degrees.

Figure 5:
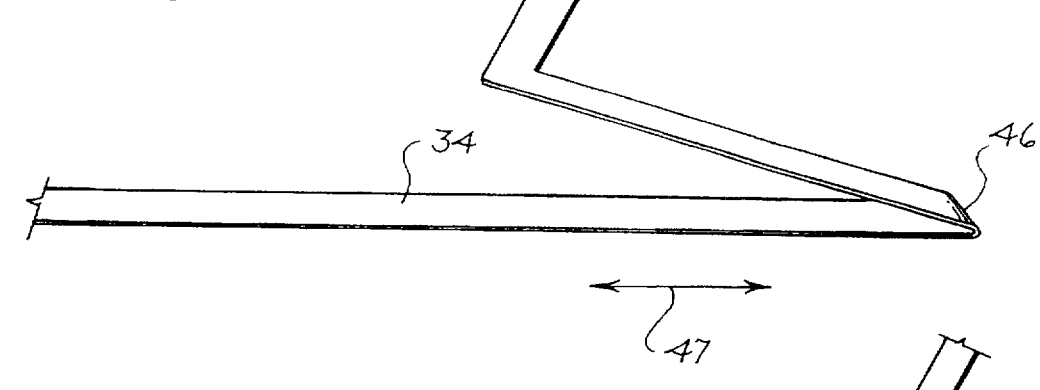

As shown in FIG. 5, the first step is to fold the flexible circuit 34 along a first fold 46. This first fold 46 is oriented at 45 degrees to the axis 47.

Figure 6:
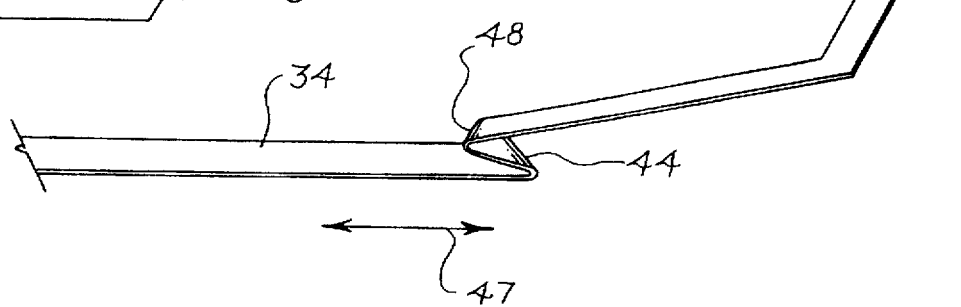

As shown in FIG. 6, the next step in the folding of the flexible circuit 34 is to form a second fold 48. This second fold 48 is preferably formed at an angle of 90 degrees with respect to the axis 47.

Figure 7:
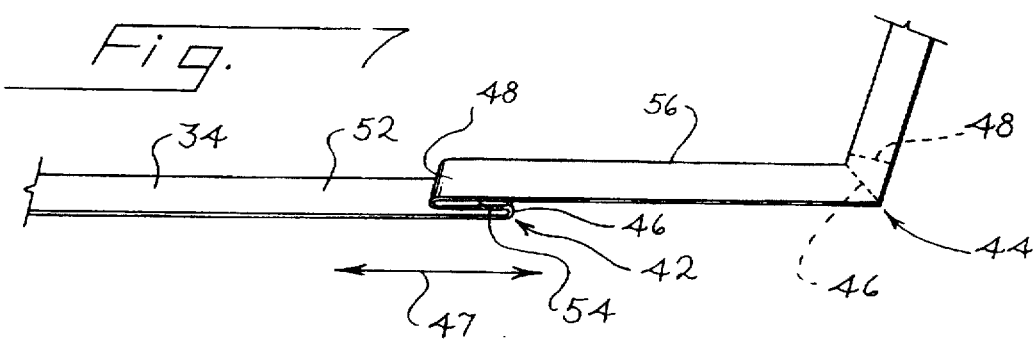

FIG. 7 shows the resulting geometry in which the conductors in first, second and third portions 52, 54, 56 of the flexible circuit 34 are all parallel to one another and parallel to the axis 47. Note that the first and second portions 52, 54 meet at the first fold 46 and that the second and third portions 54, 56 meet at the second fold 48.

Figure 8:
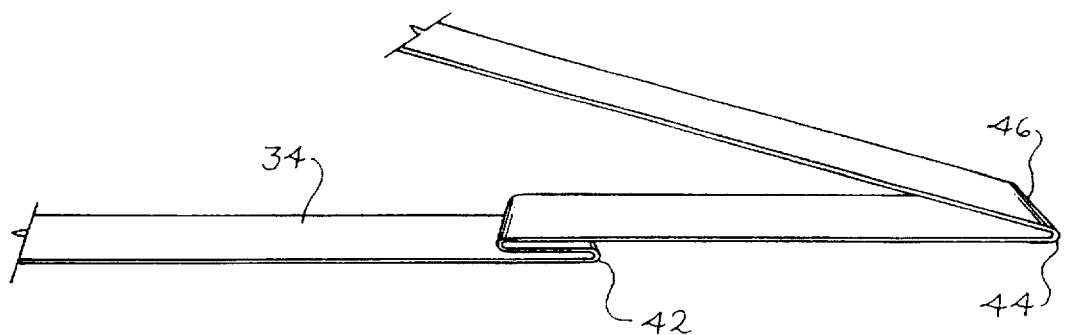
Figure 9:
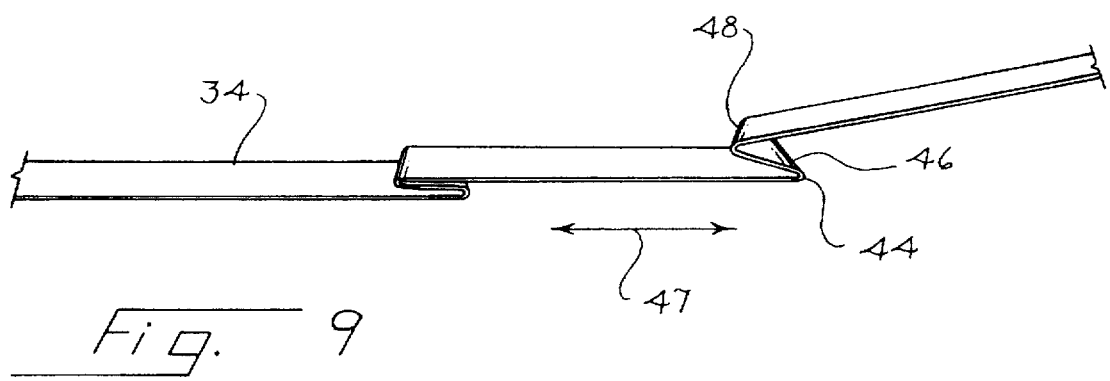
Figure 10:
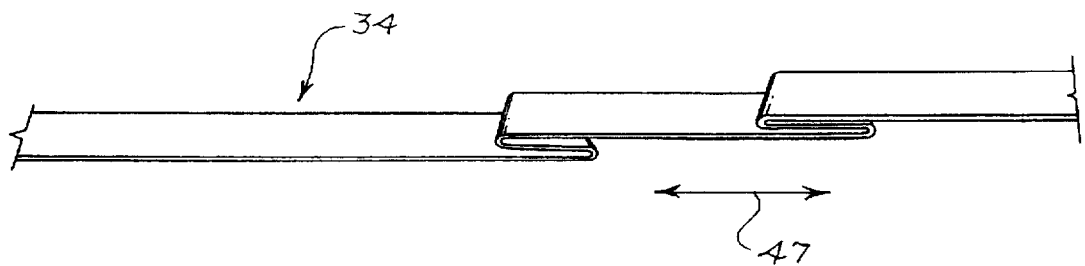

FIGS. 8 and 9 show the formation of similar first and second folds 46, 48 at the second corner 44, and FIG. 10 shows the resulting folded flexible circuit 34. Note that in the circuit 34 of FIG. 10, the conductors remain parallel to the axis 47 throughout the length of the flexible circuit 34. In alternative embodiments, the first fold 46 can be placed at 90 degrees to the axis 47 and the second fold 48 can be placed at 45 degrees to the axis 47. With this arrangement the conductors in the second portion 54 may be oriented perpendicular to the axis 47, but an elongated flexible circuit is nevertheless obtained.

Figure 11:
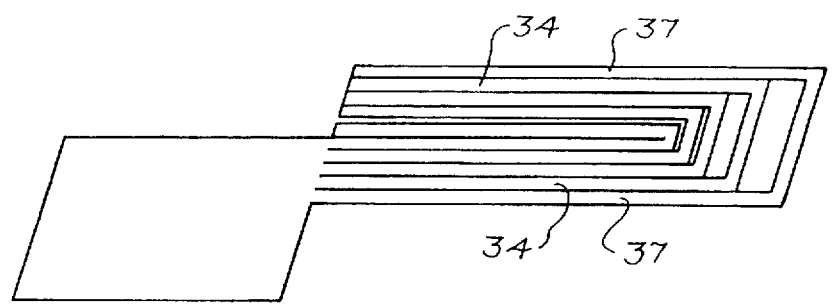
FIGS. 11–12 are two consecutive views showing the folding of the flexible circuits of the embodiment of FIG. 1.
Figure 12:
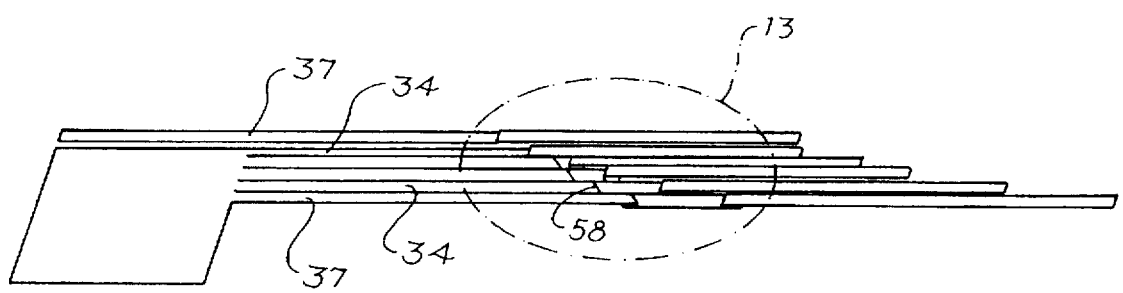
Figure 13:
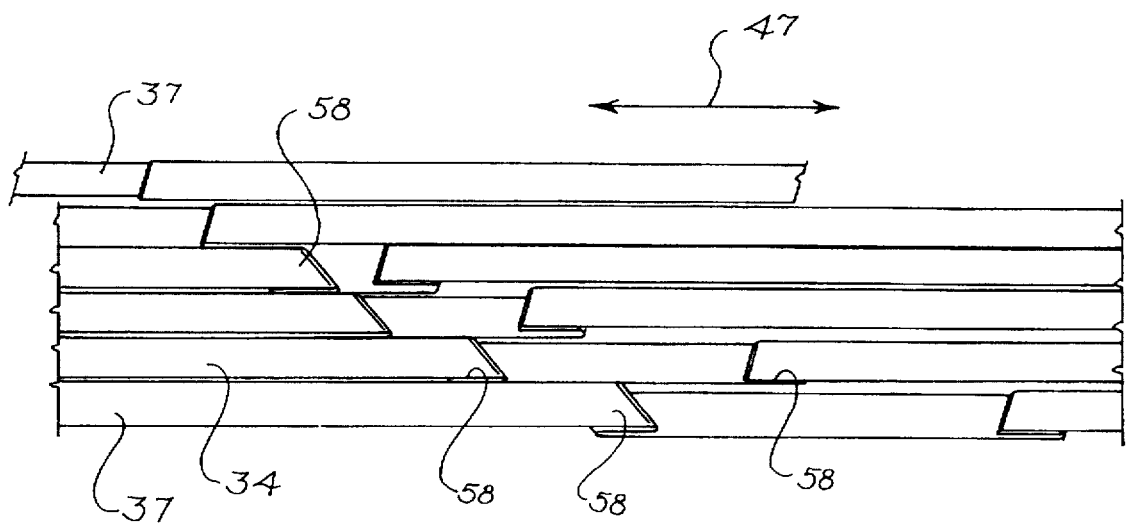
FIG. 13 is an enlarged view of a portion of FIG. 12, showing the manner in which the folded regions are axially offset from one another.

FIGS. 11–13 are schematic views showing the relationship of the folded regions among the six separate flexible circuits 34 and 37. It will be recognized that FIGS. 11–13 are schematic, and that they show only a portion of the flexible circuits shown in FIG. 3. As shown in FIGS. 12 and 13, the folded regions 58 are staggered from one another along the length of the axis 47. This means that when the six flexible circuits 34 of FIGS. 12 and 13 are stacked one on top of the other in the lumen (FIG. 2), the total thickness of the stack never exceeds eight thicknesses of the flexible circuit 34. Since the minimum thickness of the stack in regions having no folds is six, the folds do not substantially increase the overall thickness of the stack of flexible circuits. If desired, the folded regions 58 can be maintained in a folded position by any suitable adhesive or other method. Cyano-acrylate adhesive has been found suitable.

The upper and lower flexible circuits 37 preferably have uninterrupted bands of grounded copper having no traces formed thereon, as schematically shown in FIG. 2. These copper bands serve as shields placed at the top and bottom of the final folded flex circuit bundle to reduce EMI interference, and they are preferably not connected to the transducer elements. The flexible circuits are preferably folded accordion-style near the connector regions 38, 40 (FIG. 3), so that the separate bands of flexible circuit will lie on top of one another.

Figure 14:
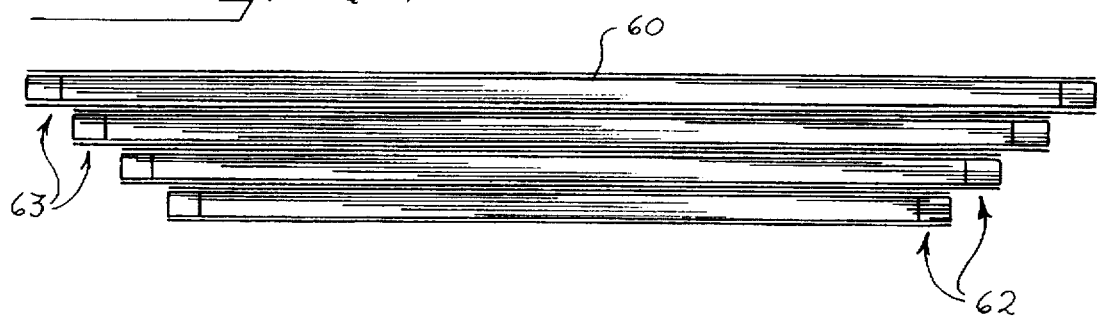
FIG. 14 is a plan view of an alternative flexible circuit suitable for use in the embodiment of FIG. 1.

FIGS. 14 through 18 relate to a second preferred embodiment of a flexible circuit 60 suitable for making an elongated circuit for interconnecting the transducer elements 26 to the control mechanism 12 of FIG. 1. FIG. 14 shows a plan view of the original layout of four flexible circuits 60 on a substrate. Each of the flexible circuits 60 includes two end portions 62, 63, and one of the end portions 62 is shown in greater detail in FIG. 15.

Figure 15:
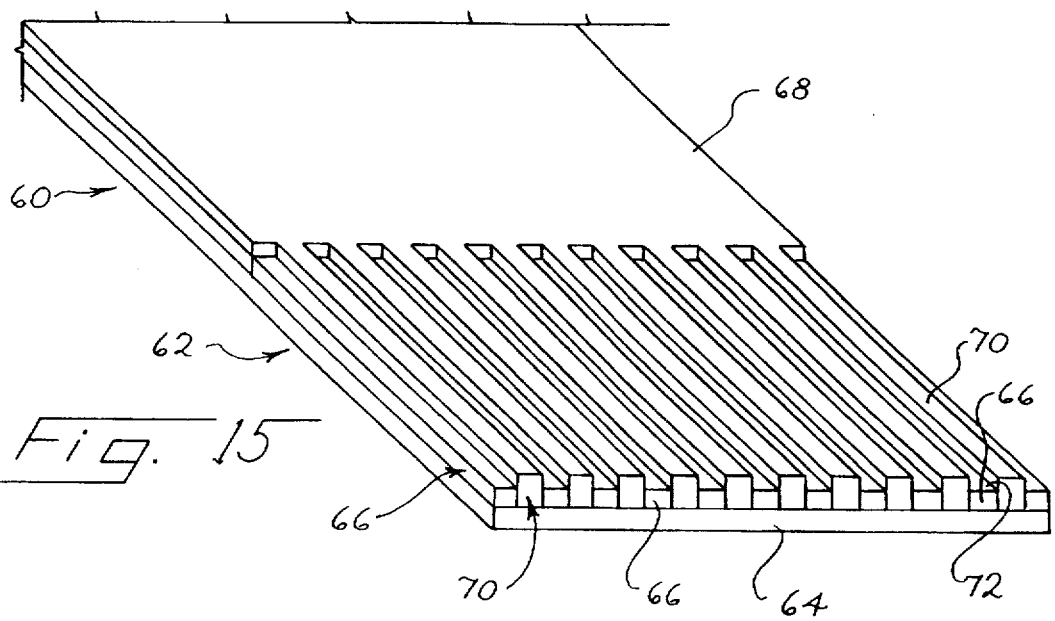
FIG. 15 is an enlarged perspective view of an end portion of one of the flexible circuits of FIG. 14.

As shown in FIG. 15, the flexible circuit 60 includes a lower insulating substrate 64, an array of insulated conductors 66, and an upper insulating layer 68. The insulating layer 68 extends in the region between adjacent ones of the conductors 66. Preferably, the insulating layer 68 at the end portion 62 or over the entire length of the flexible circuit 60 is formed of a photo-imageable coverlay such as the material distributed by DuPont under the tradename Pyralux P.C. This photo-imageable coverlay replaces the standard insulating material (such as polyimide) in this region of the flexible circuit 60. The insulating material 68 is exposed through a suitable mask (not shown) to ultraviolet light, which cross links the polymer. The insulating material that has not been cross linked is then washed away in a mildly basic aqueous solution to expose the conductors 66 at the end portion 62, while leaving thin strips or ridges 70 of insulating material between the conductors 66. The circuits are then placed in an oven at elevated temperature to cure the photo-imageable coverlay material. In effect, the ridges 70 form grooves 72 aligned with and exposing the respective conductors 66.

Figure 16:
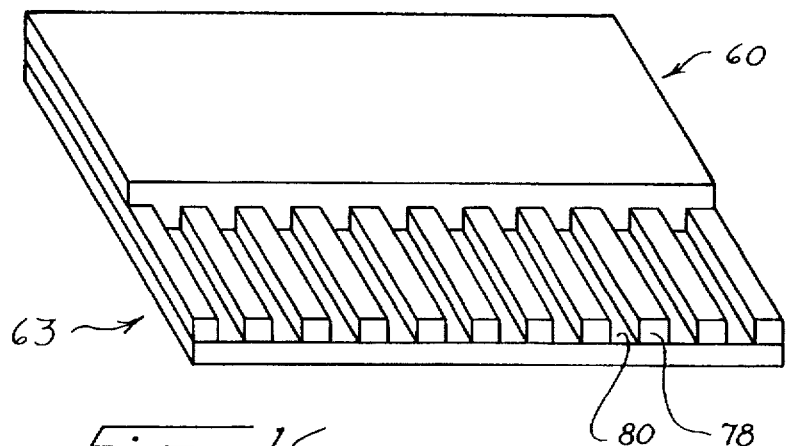
FIG. 16 is a perspective view of a portion of a mating additional circuit suitable for use with the circuit of FIG. 15.

As shown in FIG. 16, in the end portion 63 of a mating flexible circuit 60 the conductors 78 are exposed and grooves 80 are formed between adjacent conductors 78.

Figure 17:
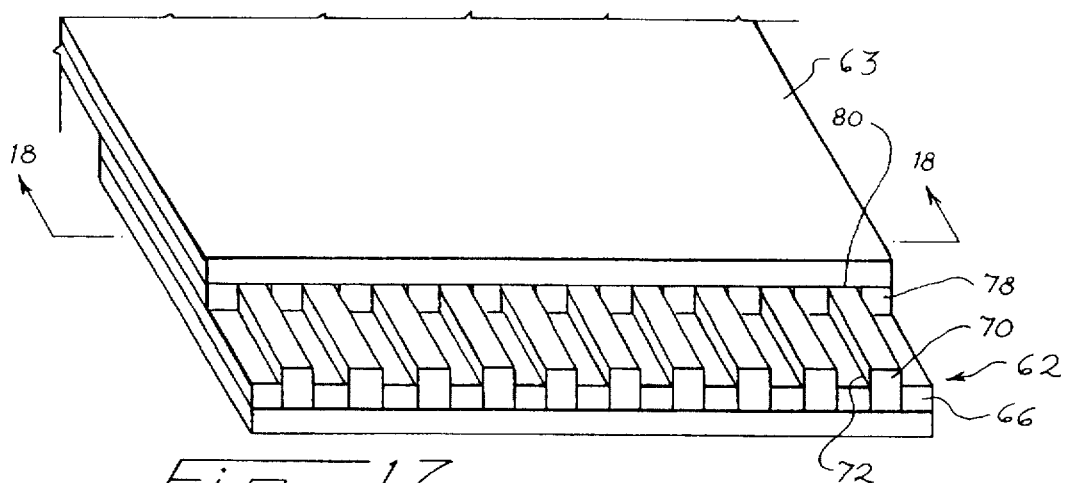
FIG. 17 is a perspective view showing the circuits of FIGS. 15 and 16 in a mated configuration.
Figure 18:
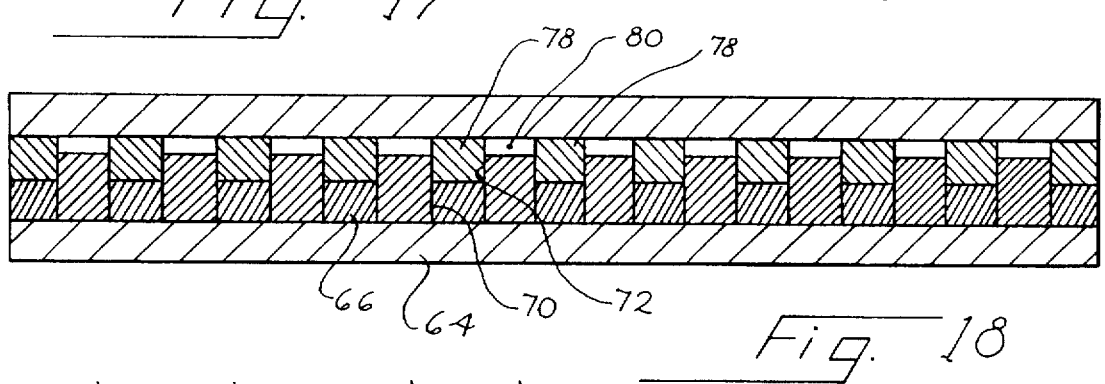
FIG. 18 is a cross-sectional view taken along line 18—18 of FIG. 17.

In order to form an elongated flexible circuit, the end portions 62, 63 are mated as shown in FIGS. 17 and 18, and then bonded or soldered together to electrically interconnect the conductors 66, 78. Note that the ridges 70 fit into grooves 80 between the conductors 78, and that the conductors 78 fit into grooves 72 between the ridges 70. In this way, the conductors 66, 78 are automatically aligned and brought into face-to-face contact. This provides a quick, efficient, and reliable method for interconnecting the conductors 66 with the conductors 78 while substantially preventing short circuits, open circuits, and miswires. Note that the ridges 70 have a height which is less than the combined heights of the conductors 66, 78. This arrangement provides complete contact between the conductors 66, 78. Once the conductors are positioned as shown in FIGS. 17 and 18, they can be secured together to obtain reliable electrical contact, and the comb pattern of interlocking ridges keeps precise alignment of the conductors. Any suitable securing technique can be used, including soldering, welding, bonding, and securing with conductive or non-conductive adhesive. It is important to recognize that the embodiment of FIGS. 14–18 eliminates the need for precise tooling or locating devices for holding the conductors in alignment while they are bonded or soldered.

In the arrangement shown in FIG. 14 the four flexible circuits 60 are provided with ends that are staggered from one another along the axial direction. Two such circuits can be bonded together such that the overlap at any location will be no more than one additional thickness of flexible circuit, plus the thickness of solder or adhesive.

Figure 19:
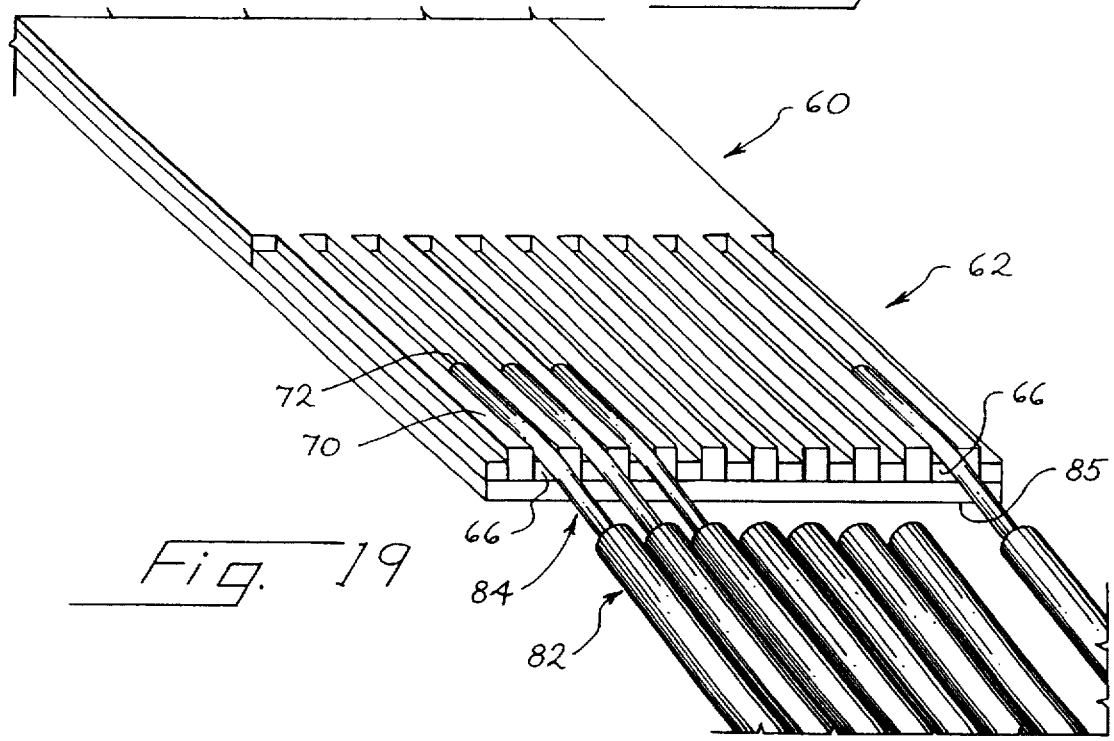
FIG. 19 is a perspective view showing the flexible circuit of FIG. 15 mated with conductors of a ribbon cable and individually insulated conductors.

FIG. 19 shows a third embodiment in which the flexible circuit 60 having the end portion 62 described and shown above in connection with FIG. 15 is connected to a miniature ribbon cable 82 that has a plurality of additional conductors 84. In the embodiment of FIG. 19, individual ones of the stripped conductors 84 are placed in the grooves 72 over respective conductors 66. The ridges 70 form physical barriers that align the conductors 84 with the conductors 66. Once aligned, the conductors 84 can be soldered, bonded, thermosonically welded, or adhesively secured with either conductive or non-conductive adhesive to the conductors 66 to obtain desired electrical contact. If desired, an individually-insulated conductor 85 may be secured with any of these techniques to one of the conductors 66, as shown in FIG. 19.

As yet another alternative, the circuit folding techniques described above in conjunction with FIGS. 4–13 can be used in combination with the alignment techniques described above in conjunction with FIGS. 14–19 to form an elongated circuit suitable for mounting in the lumen 30 of the conduit 22 (FIG. 2).

The preferred embodiments described above provide a number of important advantages. They allow assembly of an elongated flexible circuit having a length greater than 19 inches in length. This is achieved while using a thin, insulating, adhesiveless substrate for the flexible circuit, which preferably is formed of polyimide having a thickness of less than 0.001 inch (preferably 0.0005 inch) and an electrically conductive material (preferably copper) having a thickness of about 0.0009 inch and a pitch between adjacent conductors of less than or equal to 0.004 inches. The pitch is defined as the distance from the center of one conductor to the center of the adjacent conductor, including the intervening space. All of the techniques described above achieve these results while minimizing the overall thickness of a bundle of the flexible circuits. As described above, a flexible circuit having a small pitch can readily be assembled to another similar flexible circuit without complicated alignment tooling. Similarly, a small pitch ribbon cable can be attached to a flexible circuit without the use of complicated alignment tooling.

Of course, it should be understood that a wide range of changes and modifications can be made to the preferred embodiments described above. The first, second, and third embodiments describe above can be combined in any desired combination. Dimensions and materials can all be modified as appropriate for the particular application. For example, the ridges 70 described above can also be made by aligning a silk-screen template to the flexible circuit panel, wherein the template has openings to form the grooves between the ridges. A polyamic acid solution is then applied through the silk screen to create the ridges. This invention can also be adapted for use in laparaoscopic devices. The set of flexible circuits in the lumen that are connected to the transducers may include as few as one flexible circuit, or even more than the four illustrated in FIG. 2.

It is therefore intended that the foregoing detailed description be regarded as an illustration of a few of the many forms that the invention can take. It is only the following claims, including all equivalents, that are intended to define the scope of this invention.

We claim:

1. In an ultrasonic transducer assembly of the type comprising:

an elongated conduit comprising a distal end portion, a proximal end portion, and a lumen, said lumen defining an axis;

a plurality of ultrasonic transducer elements carried by the conduit adjacent the distal end portion; and a plurality of flexible circuits carried in the lumen, said plurality of flexible circuits comprising a set of flexible circuits, each flexible circuit in the set comprising a plurality of elongated conductors, at least some of said conductors electrically coupled to respective ones of the transducer elements;

the improvement comprising:

each flexible circuit in the set comprising first, second and third portions, said first and second portions meeting at a first fold, and said second and third portions meeting at a second fold, said first and third portions extending through respective, axially-spaced portions of the lumen, at least one of the folds oriented obliquely to the axis.

2. In an ultrasonic transducer assembly of the type comprising:

an elongated conduit comprising a distal end portion, a proximal end portion, and a lumen, said lumen defining an axis;

a plurality of ultrasonic transducer elements carried by the conduit adjacent the distal end portion; and a plurality of flexible circuits carried in the lumen, said plurality of flexible circuits comprising a set of flexible circuits, each flexible circuit in the set each comprising a plurality of elongated conductors, at least some of said conductors electrically coupled to respective ones of the transducer elements;

the improvement comprising:

each flexible circuit in the set comprising first, second and third portions, said first and second portions meeting at a first fold, said second and third portions meeting at a second fold, said conductors in the first portion extending generally parallel to the conductors in the third portion, said first and third portions extending through respective, axially spaced portions of the lumen, at least one of the folds oriented obliquely to the axis.

3. The invention of claim 1 or 2 wherein one of the folds is oriented obliquely to the axis, and wherein the other of the folds is oriented substantially transverse to the axis.

4. The invention of claim 3 wherein said one of the folds is oriented at about 45° to the axis.

5. The invention of claim 1 or 2 wherein the flexible circuits in the set each comprise an insulating substrate having a thickness no greater than about 0.001 inch.

6. The invention of claim 5 wherein the conductors are mounted on the substrate with a pitch no greater than about 0.004 inch.

7. The invention of claim 1 or 2 wherein the conductors are oriented substantially parallel to the axis in the first, second, and third portions of the flexible circuit.

8. The invention of claim 1 or 2 wherein the set of flexible circuits comprises a plurality of flexible circuits, and wherein the folds are positioned such that the second portions are all axially spaced from one another in the lumen.

9. In an ultrasonic transducer assembly of the type comprising:

an elongated conduit comprising a distal end portion, a proximal end portion, and a lumen, said lumen defining an axis;

a plurality of ultrasonic transducer elements carried by the conduit adjacent the distal end portion, a plurality of flexible circuits carried in the lumen, said plurality of flexible circuits comprising a set of flexible circuits, each flexible circuit in the set comprising a plurality of elongated conductors, at least some of said conductors electrically coupled to respective ones of the transducer elements;

each flexible circuit in the set comprising an end portion, each end portion comprising a plurality of substantially parallel grooves, each groove aligned with and exposing a respective one of the conductors; and a plurality of additional conductors, each of the additional conductors extending into a respective one of the grooves and electrically connected to the respective first-mentioned conductor.

10. The invention of claim 9 wherein the additional conductors are included in at least one additional flexible circuit.

11. The invention of claim 10 wherein said end portion of each first-mentioned flexible circuit in the set comprises a plurality of ridges oriented parallel to the grooves, and wherein each additional flexible circuit comprises a plurality of recesses, said recesses extending parallel to and between the additional conductors, said ridges received in said recesses.

12. The invention of claim 9 wherein the additional conductors comprise individually insulated conductors.

13. The invention of claim 9 wherein at least some of the additional conductors are included in a ribbon cable.

14. The invention of claim 9 wherein each flexible circuit in the set further comprises first, second and third portions, said first and second portions meeting at a first fold, said second and third portions meeting at a second fold, said conductors in the first portion extending generally parallel to the conductors in the third portion, said first and third portions extending through respective, axially spaced portions of the lumen.

15. The invention of claim 14 wherein at least one of the folds is oriented obliquely to the axis.

16. The invention of claim 15 wherein one of the folds is oriented obliquely to the axis, and wherein the other of the folds is oriented substantially transverse to the axis.

17. The invention of claim 16 wherein said one of the folds is oriented at about 45° to the axis.

18. The invention of claim 9 wherein said first-mentioned conductors are bonded to respective ones of the additional conductors to obtain electrical contact.

19. The invention of claim 9 wherein said first-mentioned conductors are joined with an adhesive to respective ones of the additional conductors to obtain electrical contact, said adhesive elected from the group consisting of conductive adhesive and non-conductive adhesive.

20. The invention of claim 9 wherein said first-mentioned conductors are joined by welding to respective ones of the additional conductors to obtain electrical contact.

21. The invention of claim 9 wherein said first-mentioned conductors are soldered to respective ones of the additional conductors to obtain electrical contact.

22. The invention of claim 9 wherein the set of flexible circuits comprises a plurality of flexible circuits, and wherein the end portions are all axially spaced from one another in the lumen.

23. In an ultrasonic transducer assembly of the type comprising:

an elongated conduit comprising a distal end portion, a proximal end portion, and a lumen, said lumen defining an axis;

a plurality of ultrasonic transducer elements carried by the conduit adjacent the distal end portion; and a set of flexible circuits carried in the lumen, each flexible circuit of the set comprising a plurality of elongated conductors, at least some of said conductors electrically coupled to respective ones of the transducer elements;

the improvement comprising:

each flexible circuit in the set comprising first, second and third portions, said first and second portions meting at a first fold, and said second and third portions meeting at a second fold, said first and third portions extending through respective, axially-spaced portions of the lumen; and first and second shielding layers carried in the lumen, said set of flexible circuits disposed between the shielding layers such that the shielding layers provide EMI shielding, said shielding layers each comprising a respective shielding flexible circuit.

24. In an ultrasonic transducer assembly of the type comprising:

an elongated conduit comprising a distal end portion, a proximal end portion, and a lumen, said lumen defining an axis; and a plurality of ultrasonic transducer elements carried by the conduit adjacent the distal end portion;

the improvement comprising:

a plurality of flexible circuits carried in the lumen, said flexible circuits comprising a plurality of elongated conductors and each flexible circuit comprising a respective band, at least some of said conductors electrically coupled to respective ones of the transducer elements;

said flexible circuits folded accordion-style near at least one end of the flexible circuits so that the separate bands of the flexible circuits lie on top of one another.

25. The invention of claim 24 wherein the flexible circuits are folded accordion-style near both ends of the flexible circuit.

26. The invention of claim 24 wherein the flexible circuits lie on top of one another where they are folded accordion-style.

27. The invention of claim 24, wherein each flexible circuit comprises first, second and third portions, said first and second portions meeting at a first fold, and said second and third portions meeting at a second fold, said first and third portions extending through respective, axially-spaced portions of the lumen.

28. In an ultrasonic transducer assembly of the type comprising:

- an elongated conduit comprising a distal end portion, a proximal end portion, and a lumen, said lumen defining an axis;
- a plurality of ultrasonic transducer elements carried by the conduit adjacent the distal end portion; and
- a plurality of flexible circuits carried in the lumen, said plurality of flexible circuits comprising a set of flexible circuits, each flexible circuit in the set comprising a plurality of elongated conductors, at least some of said conductors electrically coupled to respective ones of the transducer elements;

the improvement comprising:

each flexible circuit in the set comprising first, second and third portions, said first and second portions meeting at a first fold, and said second and third portions meeting at a second fold, said first and third portions extending through respective, axially-spaced portions of the lumen, first and second folds of a flexible circuit of said plurality of flexible circuits being staggered with respect to first and second folds of an adjacent flexible circuit of said plurality of flexible circuits.

29. In an ultrasonic transducer assembly of the type comprising:

- an elongated conduit comprising a distal end portion, a proximal end portion, and a lumen, said lumen defining an axis;
- a plurality of ultrasonic transducer elements carried by the conduit adjacent the distal end portion; and
- a plurality of flexible circuits carried in the lumen, said plurality of flexible circuits comprising a set of flexible circuits, each flexible circuit in the set comprising a plurality of elongated conductors, at least some of said conductors electrically coupled to respective ones of the transducer elements;

the improvement comprising:

each flexible circuit in the set comprising first, second and third portions, said first and second portions meeting at a first fold, and said second and third portions meeting at a second fold, said first and third portions extending through respective, axially-spaced portions of the lumen, each flexible circuit being characterized by a thickness and said plurality of flexible circuits being characterized by a maximum thickness, said maximum thickness being about a sum of the thickness of each flexible circuit of said plurality of flexible circuits plus twice the thickness of one flexible circuit of said plurality of flexible circuits.

30. The invention of claim 23, wherein first and second folds of a flexible circuit of said set of flexible circuits are staggered with respect to first and second folds of an adjacent flexible circuit of said set of flexible circuits.

31. The invention of claim 23, wherein each flexible circuit is characterized by a thickness and said set of flexible circuits is characterized by a maximum thickness, and wherein said maximum thickness is about a sum of the thickness of each flexible circuit of said set of flexible circuits plus twice the thickness of one flexible circuit of said set of flexible circuits.

32. The invention of claim 1 or 2, wherein a single axis passes through said first, second, and third portions of each flexible circuit.

33. The invention of claim 32, wherein a total flexible circuit thickness through said single axis is less than about a sum of four individual flexible circuit thicknesses.

34. The invention of claim 1 or 2, wherein first and second folds of a flexible circuit of said plurality of flexible circuits are staggered with respect to first and second folds of an adjacent flexible circuit of said plurality of flexible circuits.

35. The invention of claim 1 or 2, wherein each flexible circuit is characterized by a thickness and said plurality of flexible circuits is characterized by a maximum thickness, and wherein said maximum thickness is about a sum of the thickness of each flexible circuit of said plurality of flexible circuits plus twice the thickness of one flexible circuit of said plurality of flexible circuits.

* * * * *